United States Patent
Hsieh et al.

(10) Patent No.: US 8,313,949 B2
(45) Date of Patent: Nov. 20, 2012

(54) DETECTING PHOSPHOLIPIDOSIS AND DIAGNOSING LYSOSOMAL STORAGE DISORDERS

(75) Inventors: Frank Hsieh, Lexington, MA (US); Elizabeth Tengstrand, Belmont, MA (US)

(73) Assignee: Nextcea Inc., Woburn, MA (US)

( * ) Notice: Subject to any disclaimer, the term of this patent is extended or adjusted under 35 U.S.C. 154(b) by 452 days.

(21) Appl. No.: 12/579,121

(22) Filed: Oct. 14, 2009

(65) Prior Publication Data

US 2010/0267061 A1    Oct. 21, 2010

Related U.S. Application Data

(60) Provisional application No. 61/169,789, filed on Apr. 16, 2009.

(51) Int. Cl.
- G01N 33/53 (2006.01)
- G01N 33/92 (2006.01)
- G01N 33/50 (2006.01)
- C12Q 1/02 (2006.01)
- C12Q 1/00 (2006.01)

(52) U.S. Cl. ............ 436/71; 435/7.92; 435/29; 435/7.1; 435/4

(58) Field of Classification Search .............. 436/71; 435/7.2, 7.9, 7.1, 4
See application file for complete search history.

(56) References Cited

U.S. PATENT DOCUMENTS

| | | |
|---|---|---|
| 2007/0166829 A1 | 7/2007 | Horinouchi et al. |
| 2007/0202487 A1 | 8/2007 | Fan |
| 2007/0218460 A1 | 9/2007 | Takami et al. |

OTHER PUBLICATIONS

Baronas et al., Biomarkers to monitor drug-induced phospholipidosis, Toxicology and Applied Pharmacology, 2007, 218, pp. 72-78.*
Anderson, Nora and Jurgen Borlak, "Drug-Induced Phospholipidosis," FEBS Letters, 580:5533-5540 (2006).
Hullin-Matsuda et al., "Bis(monoacylglycero)phosphate, A Peculiar Phospholipid to Control the Fate of Cholesterol: Implications in Pathology," Prostglandins, Leukotrienes and Essential Fatty Acids (2009), doi:10.1016/j.plefa.2009.09.006.
Matsuo et al., "Role of LBPA and Alix in Multivesicular Liposome Formulation and Endosome Organization," Science, 303:531-534 (2004).
Nakashima et al., "A Mouse Model for Niemann-Pick Disease: Phospholipid Class and Fatty Acid Composition of Various Tissues," Journal of Lipid Research, 25:219-227 (1984).
Reasor et al. "Drug-Induced Phospholipidosis: Are There Functional Consequences?" Exp Biol Med., 226(9):825-830 (2001).

* cited by examiner

*Primary Examiner* — Christine T Mui
(74) *Attorney, Agent, or Firm* — Occhiuti Rohlicek & Tsao LLP

(57) ABSTRACT

Disclosed are methods for evaluating the potential or activity of a test compound to induce phospholipidosis in a target subject, for managing patient treatment, and for diagnosing a lysosomal storage disorder in a human subject.

20 Claims, 9 Drawing Sheets

Phosphatidylglycerol 3 mono-22:6-BMP        2 mono-22:6-BMP

5A

5B

8A
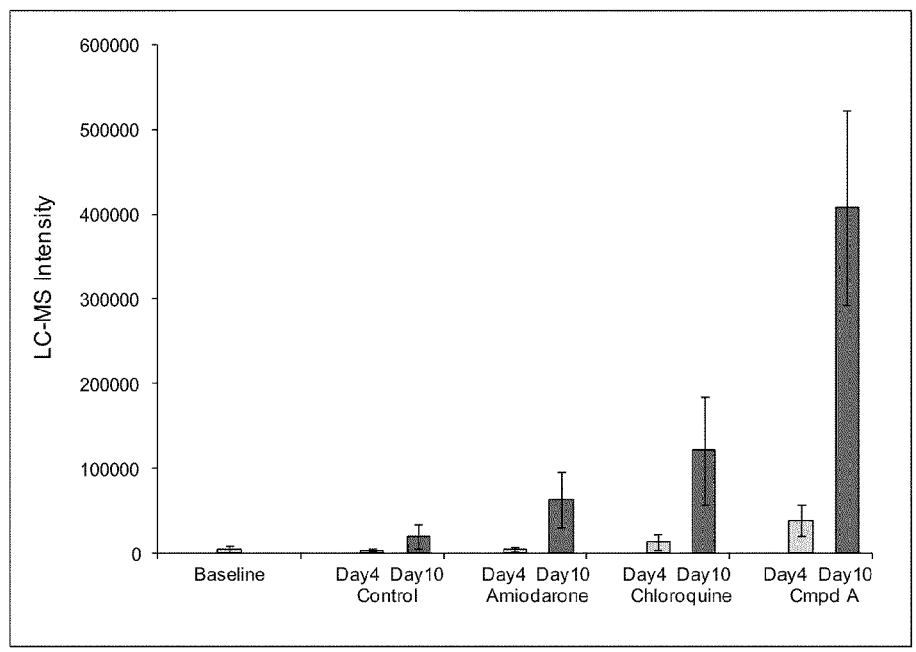
8B
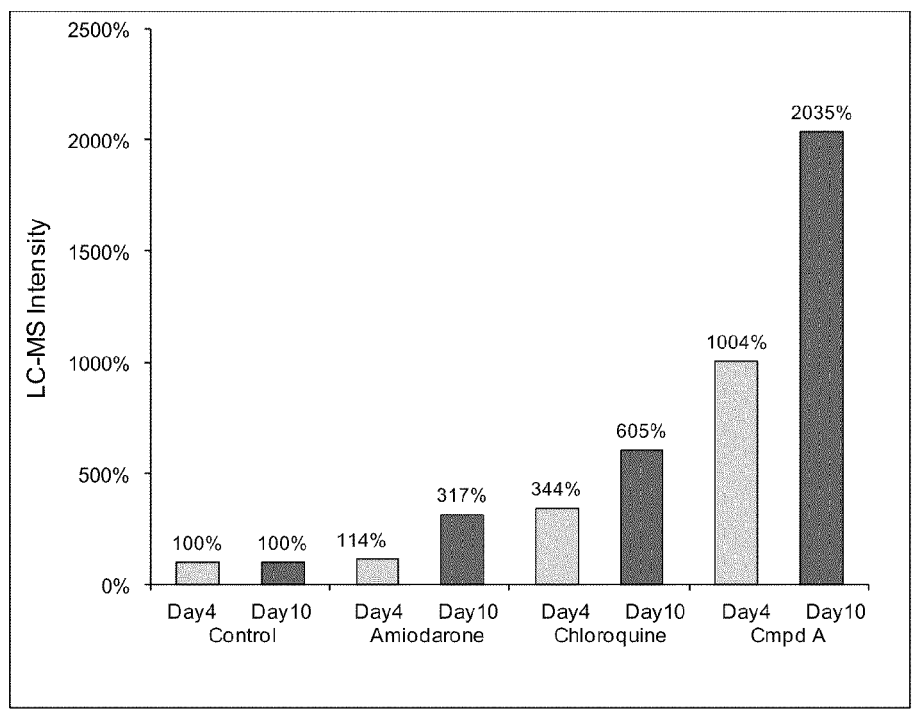
FIGs. 8A and B

DETECTING PHOSPHOLIPIDOSIS AND DIAGNOSING LYSOSOMAL STORAGE DISORDERS

RELATED APPLICATION

This application claims priority of U.S. Provisional Application No. 61/169,789, filed Apr. 16, 2009, the content of which is incorporated herein by reference in its entirety.

BACKGROUND

Drug-induced phospholipidosis is a lysosomal storage disorder characterized by the excess accumulation of phospholipids in cells and tissues. Phospholipidosis is a common finding in toxicity studies of cationic amphiphilic drugs (CADs) in both animals and humans and has become a significant regulatory concern. Major concerns for regulatory agencies are drug-induced phospholipidosis of the liver, kidneys, muscle, heart, and lung tissues, which could contribute to the adverse effects of drugs in these organs. The morphological effects of drug-induced phospholipidosis in tissues resemble the whorled myelin figures in the tissues of patients with Niemann-Pick Type C (NPC) disease. NPC and other inherited lysosomal storage disorders result in the harmful accumulation of lipid materials (e.g., lipids, glycolipids, lipoproteins) in the body's cells and tissues. Over time, excessive storage of the lipid materials causes permanent cellular and tissue damage, particularly in the brain, peripheral nervous system, liver, spleen, and bone marrow.

Drug-induced phospholipidosis cannot currently be determined non-invasively. There is a need for readily accessible biomarkers to determine the onset and time course of phospholipidosis in preclinical and clinical studies and to explore the links between phospholipidosis and the toxicities of drugs.

SUMMARY

This invention is based, at least in part, on the unexpected discovery that levels of different species of di-docosahexaenoyl (22:6)-bis(monoacylglycerol)phosphate (di-22:6-BMP), di-docosahexaenoyl (C22:6)-phosphatidylglycerol (di-22:6-PG), and mono-docosahexaenoyl (22:6)-bis(monoacylglycerol)phosphate (mono-22:6-BMP) correlate differentially with the phospholipidosis induced by different drugs and inherited lysosomal storage disorders.

Accordingly, one aspect of this invention features a method for evaluating the potential or activity of a test compound (including an approved drug) to induce phospholipidosis in a target subject. The method is conducted by (a) obtaining a solution containing (1) a test sample from a test subject that has been administered a test compound or (2) a population of test cells that have been contacted with the test compound or (3) endocytic vesicles isolated from the test sample or the test cells; and (b) determining the level of a first biomarker in the test sample, cells, or endocytic vesicles. The first biomarker is selected from the group consisting of 2,2' di-22:6-BMP, 3,2' di-22:6-BMP, 2,3' di-22:6-BMP, di-22:6-PG, 2-mono-22:6-BMP, and 3-mono-22:6-BMP the structures of which are shown FIGS. 1 to 3. The test compound is determined to have the potential or activity to induce phospholipidosis in the target subject if the level of the first biomarker is at or above a pre-determined level.

When a test subject is used, the pre-determined level can be a level obtained from the test subject prior to drug treatment or an appropriate control subject that is identical to the test subject except that the control subject has not been administered the test compound. When test cells are used, the pre-determined level can be a level obtained from a control population of cells that are identical to the test population of cells except that the control cells have not been contacted with the test compound.

A "subject" refers to either a human or non-human animal. Examples of non-human animals include all vertebrates, e.g., mammals, such as non-human primates (particularly higher primates), dogs, rodents (e.g., mice, rats, or guinea pigs), pigs, cats, and non-mammals, such as birds, amphibians, reptiles, etc. In one embodiment, the subject is a human. In another embodiment, the subject is an animal that is used in drug safety assessment or a suitable animal disease model. In a preferred embodiment, the target subject is a human for evaluating the activity of a test compound to induce phospholipidosis in humans. The test subject can be a mammal, such as a rodent, dog, pig, non-human primate, or human.

Another aspect of this invention features a method for managing the treatment of a patient. Preferably, such a patient has an inherited form of, or is at risk of developing, a lysosomal storage disorder that results in the accumulation of lipid materials in affected cells and tissues (such as phospholipidosis) and related clinical side effects in response to the treatment. The method includes the steps of (1) identifying a patient under, or in need of, a treatment for a condition, (2) obtaining a test sample from the patient, and (3) determining the level of a first biomarker in the test sample. The first biomarker is selected from the group consisting of 2,2' di-22:6-BMP, 3,2' di-22:6-BMP, 2,3' di-22:6-BMP, di-22:6-PG, 2-mono-22:6-BMP, and 3-mono-22:6-BMP. The patient is determined not to be suitable for the initiation or continuation of the treatment if the level of the first biomarker is at or above a predetermined value. In one example, the pre-determined level is a level obtained from a control subject that has phospholipidosis.

In a further aspect, this invention features a method of diagnosing an inherited lysosomal storage disorder that results in lipidosis in a human or non-human subject. The method includes the steps of (1) obtaining a test sample from the subject; and (2) determining the level of a first biomarker in the test sample, where the first biomarker is selected from the group consisting of 2,2' di-22:6-BMP, 3,2' di-22:6-BMP, 2,3' di-22:6-BMP, di-22:6-PG, 2-mono-22:6-BMP, and 3-mono-22:6-BMP. An increased expression level of the first biomarker relative to a pre-determined level is indicative of the lysosomal storage disorder or a predisposition for developing the disorder in the future. In particular, this method can be used in order to determine whether a human subject is affected by or at risk of developing Niemann-Pick Type C (NPC) disease or another type of lysosomal lipidosis, such as neuronal ceroid lipofuscinosis or phospholipidosis. In the case of the NPC disease, the pre-determined level of the first biomarker is a level obtained from a control subject that is affected by the NPC disease.

In one example, each of the above-described methods can further include a step of comparing the level of the first biomarker with the pre-determined level. In another, each method further includes a step of separating 2,2' di-22:6-BMP, 3,2' di-22:6-BMP, 2,3' di-22:6-BMP, di-22:6-PG, 2-mono-22:6-BMP, and 3-mono-22:6-BMP from each other before determining the level of the first biomarker. For example, one can separate two, three, or all of the markers, e.g., using liquid chromatography coupled with mass spectrometry (LC-MS) in order to evaluate the level of each marker individually (as shown in FIG. 4). The determining step can be conducted by LC-MS, LC-MS/MS, GC/MS, GC/MS/MS, or ELISA.

In each method, the test sample can be a whole blood sample, plasma sample, serum sample, urine or urinary sediment sample, broncheoalveolar lavage fluid sample, lymph sample, cerebrospinal fluid sample, saliva sample, semen sample, breast milk sample, or feces sample. The test sample can also be a tissue sample from liver, kidney, muscle, heart, lung, spleen, lymph node, bone marrow, skin, blood vessels and valves, eye, or brain. In one embodiment, the population of the test cells can include broncheoalveolar lavage cells, erythrocytes, white blood cells, nerve cells, liver cell fractions, skin fibroblasts, bone marrow histiocytes, chorionic villus cells, retinal pigment epithelial cells, or amniotic fluid cells. The test sample can also be isolated endocytic vesicles, such as endosomes, lysosomes, and exosomes derived from cells and tissues. In another embodiment, the test cells are cells of human hepatocellular carcinoma cell line (HepG2), diploid rat liver epithelial cell line (ARLJ301-3), Chinese hamster lung cell line (CHL/IU), baby hamster kidney cells (BHK), human kidney adenocarcinoma cells (human 769-P), human kidney proximal tubular cells (HK-2), or mouse macrophage-like cell line (J744A).

Each of the above-described methods can further include a step of determining the level of a second biomarker of phospholipidosis. This second biomarker can be a lipid or a protein as disclosed below. In one example, each of the above-described methods can further include a step of determining the levels of other phospholipids, such as different species of phosphatidylinositol (PI), phosphatidylcholine (PC), phosphatidylethanolamine (PE), phosphatidylglycerol (PG), phosphatidylserine (PS), phosphatidic acid (PA), or other types of lipid materials, including lysophospholipids, sphingolipids, glycolipids, cholesterol, lipoproteins etc. In a second example, each method can further include a step of determining the levels of proteins associated with cellular degradation pathways and lysosomal function, such as LC3, Beclin-1, Niemann-Pick C1 and C2 proteins (NPC1 and NPC2), and annexin II. In another example, the above-described methods can further include a step of determining the levels of additional species of BMP, the levels of total BMP, or the fatty acid classification of total BMP.

The details of one or more embodiments of the invention are set forth in the accompanying drawings and description below. Other features, objects, and advantages of the invention will be apparent from the description and drawings, and from the claims.

DESCRIPTION OF DRAWINGS

FIGS. 8A and 8B are diagrams showing levels of 2,2' di-C22:6-BMP in urine samples from Sprague-Dawley rats that received treatments of control, amiodarone (150 mg/kg/day), chloroquine (120 mg/kg/day), or Compound A (50 mg/kg/day).

DETAILED DESCRIPTION

Figure 1:
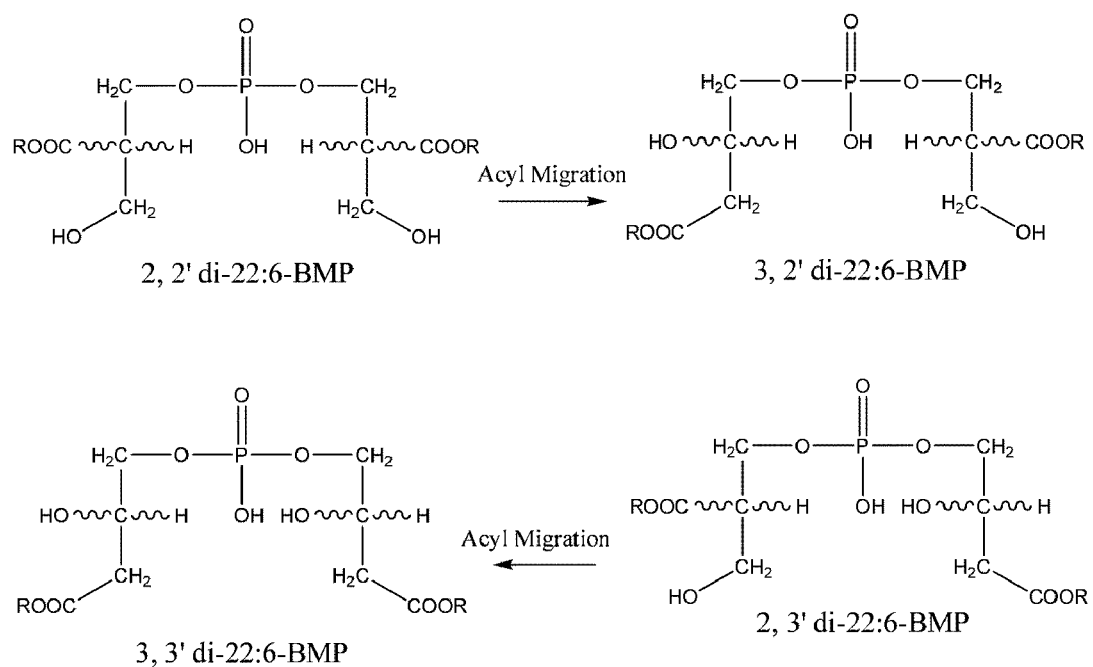
FIG. 1 is a diagram showing structures of di-C22:6-BMP species, where R is aliphatic alkenyl (C22:6, C18:1, or C18:2).
Figure 2:
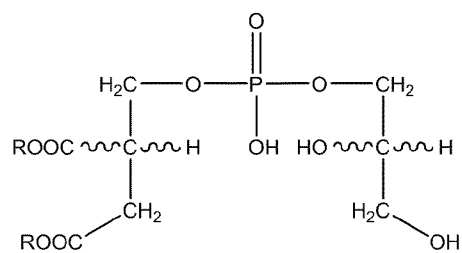
FIG. 2 is a diagram showing the structure of di-docosahexaenoyl (C22:6)-phosphatidylglycerol (di-22:6-PG), where R is aliphatic alkenyl (C22:6, C18:1, or C18:2).
Figure 3:
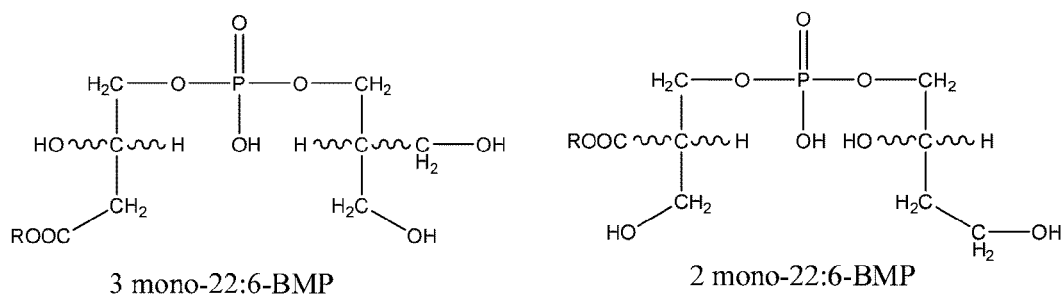
FIG. 3 is a diagram showing the structure of mono-docosahexaenoyl (22:6)-bis(monoacylglycerol)phosphate (mono-22:6-BMP), where R is aliphatic alkenyl (C22:6, C18:1, or C18:2).

This invention is based, at least in part, on the unexpected discovery that the levels of different species of di-22:6-BMP, di-22:6-PG, and mono-22:6-BMP correlate differentially with the phospholipidosis induced by different drugs and inherited lysosomal storage disorders, such as the NPC disease.

Drug-Induced Phospholipidosis

Drug-induced phospholipidosis is a phospholipid storage disorder that results in the excessive accumulation of phospholipids in tissues. Various drugs can induce phospholipidosis. Among them, cationic amphiphilic drugs (CADs) can penetrate the plasma membrane and are sequestered within the lysosomes where they become trapped in the acidic environment. Other phospholipidotic compounds, such as aminoglycoside antibiotics, are delivered to the lysosomal compartment by glycoprotein receptors or after binding to negatively charged phospholipids on the cell surface. A gradual accumulation of undigested drug-phospholipid complexes and a decrease in lysosomal enzyme activities results in the intracellular accumulation of multi-lamellar (myeloid bodies) upon prolonged drug exposure.

The most well established marker of phospholipidosis is the abnormal accumulation of myeloid bodies in the cytoplasm or lysosomes of affected cells. Myeloid bodies can be visualized in thin tissue sections, peripheral blood cells, and urinary sediment using electron microscopy. They are characterized by several concentric layers of electron-dense, membranous material surrounded by a single limiting membrane. Myeloid bodies occur naturally in some tissues where they generally serve as storage vesicles for secreted or trapped lipid and protein materials within the lysosomes. In drug-induced phospholipidosis, myeloid bodies also serve as repositories for excess drug and undigested drug-phospholipid complexes.

Drug-induced phospholipidosis is a significant concern for risk assessment. Many drugs that cause phospholipidosis in animals are also associated with unwanted clinical side effects, such as drug-induced QT prolongation, myopathy, hepatotoxicity, pulmonary dysfunction, or kidney toxicity, as addressed in more detail below.

Lysosomal Storage Disorders

Myeloid bodies that occur in drug-induced phospholipidosis resemble the whorled myelin figures in the tissues of patients affected by lysosomal storage disorders including the NPC disease (Warren et al., J Vet Diagn Invest 2000; 12:483-496). NPC disease is an inherited disorder that is characterized by defects in intracellular cholesterol sorting and transport. Under normal conditions, the cholesteryl ester derived from low density lipoprotein mediates a complex feedback mechanism that stabilizes the intracellular concentration of cholesterol. In NPC patients, a defect in the activities of the NPC1 and NPC2 proteins results in a very slow efflux of unesterified cholesterol from the late endocytic compartments. The ratio of unesterified cholesterol and bis(monoacylglycerol)phosphate (BMP) is important within the internal lysosomal membrane for the efficient hydrolysis of membrane components to occur. As a result, not only cholesterol, but other membrane components (i.e., sphingomyelin, BMP, glucosylceramide, glycospingolipids, phospholipids, and glycolipids) may secondarily accumulate depending on the cellular lipid profile. The defects in lipid trafficking that occur in NPC cells can lead to cell-autonomous death.

Mechanisms of Phospholipidosis

The mechanisms that lead to the accumulation of myeloid bodies in phospholipidosis show some similarities to those observed in the etiology of NPC disease. The most well described mechanisms of phospholipidosis involve the trapping of drugs within the lysosomal compartment and a gradual accumulation of drug-phospholipid complexes within the internal lysosomal membranes. More recent hypotheses related to phospholipidosis involve drug effects on cholesterol status and miss targeting of lysosomal enzymes from the Golgi through the mannose-6-phosphate (M6PR/IGF2) receptor pathway.

Similar to NPC cells, cells that are affected by phospholipidosis are hypothesized to require large amounts of BMP within the internal lysosomal membranes for the hydrolysis of accumulated drug-phospholipid complexes and undigested membranous materials to occur. A higher than normal demand for BMP within the internal lysosomal membranes and the inhibition of phosphatidate phosphohydrolase (PA-Pase) by drugs could result in the redirection of phospholipid synthesis towards the acidic phospholipids (i.e., phosphatidylglycerol and phosphatidylinositol) which serve as the precursors for BMP synthesis. CADs are speculated to cause a NPC phenotype by binding with negatively charged phospholipids such as BMP. In addition to BMP, unesterified cholesterol and other species of phospholipids may also accumulate within the lysosomes due to direct drug inhibitory effects on lysosomal enzyme activities ($PLA_1$, $PLA_2$, PLC) or through the formation of drug-phospholipid complexes.

An increase in undigested membranous materials within phospholipidotic cells results in an abnormal accumulation of lysosomal myeloid bodies. Some of the phospholipidotic vesicles may pass through the cytoplasm and fuse with the plasma membrane on the opposite side of the cell, releasing their components into the extracellular space by exocytosis. It has been suggested that the elimination of myeloid bodies in phospholipidosis may be induced through an increased turnover of intracellular components (i.e., autophagy), which could represent an adaptive survival strategy. Alternatively, an imbalance in autophagic induction and flux could also result in autophagic stress and the trigger of autophagic cell death as observed in NPC and other lysosomal storage disorders.

Biomarkers for Phospholipidosis

As mentioned above, the conventional standard for phospholipidosis is the visual confirmation of myeloid bodies in tissues. Electron microscopy is typically used to reveal the presence of myeloid bodies in thin tissue sections from biopsy specimens, pulmonary macrophages, or peripheral blood cells. In each case, the number of myeloid bodies are averaged in different grids and compared to normal samples. Despite its utility, this electron microscopy approach is invasive, relatively non-quantitative, expensive, and time consuming. Also, it has a limited utility in defining the temporal relationship between phospholipid status and cellular function.

This invention provides an alternative and less invasive approach for detecting phospholipidosis. It employs particular species of BMP in the blood or urine as readily accessible biomarkers for the routine assessment of tissue phospholipidosis. Compared to electron microscopy, the method described herein provides a better means of defining the temporal relationship between the onset and time course of phospholipidosis with the changes that lead to drug toxicity. As a result, it provides a better means to determine whether phospholipidosis represents an adaptive or toxic manifestation.

BMP, also called lysobisphosphatidic acid (LBPA), is a lysosomal phospholipid. BMP can theoretically exist in four geometrical isoforms (FIG. 1). Individual steps of the BMP reaction sequence have been described by Amidon et al. (Biochemistry 1995; 34(16):5554-5560.) and Thornburg et al. (Journal of Biological Chemistry 1991; 266(11):6834-6840.) Amidon et al. suggested that in vivo the fatty acid chains of BMP are predominantly esterified to the β positions of the glycerol backbone (i.e., 2,2'di-22:6-BMP). Alternatively, Thornburg et al predicted that the fatty acid chains migrate to the α positions (i.e., 3,3'-BMP) because of the acidic environment of late endosomes and lysosomes.

As described herein, different species of di-22:6-BMP, di-22:6-PG, and mono-22:6-BMP correlate differentially with the tissue phospholipidosis induced by different drugs and inherited lysosomal storage disorders. Accordingly, this invention features methods of assessing the development of drug-induced tissue phospholipidosis in preclinical and clinical studies and for diagnosing lysosomal storage disorders that result in the accumulation of lipid materials within cells and tissues.

Analytical Methods

To evaluate the potential of a test compound to induce phospholipidosis in a target subject, one can obtain a test sample or population of cells from a test subject that has been administered a test compound. She or he can then determine the level of a first biomarker in the test sample or the cells. The first biomarker is selected from the group consisting of 2,2' di-22:6-BMP, 3,2' di-22:6-BMP, 2,3' di-22:6-BMP, di-22:6-PG, 2-mono-22:6-BMP, and 3-mono-22:6-BMP. The test compound is determined to have the activity to induce phospholipidosis in the target subject if the level of the first biomarker is at or above a pre-determined level. In other words, the method for the prediction of drug-induced phospholipidosis is based on the individual or combined use of isoforms of di-docosahexaenoyl (C22:6)-bis(monoacylglycerol) phosphate (i.e., 2,2'-di-22:6-BMP, 2,3'-di-22:6-BMP, 3,2'-di-22: 6-BMP, and 3,3'-di-22:6-BMP), di-docosahexaenoyl (C22: 6)-phosphatidylglycerol (di-22:6-PG), and mono-docosahexaenoyl (22:6)-bis(monoacylglycerol)phosphate (i.e., 2-mono-22:6-BMP and 3-mono-22:6-BMP).

1. Subjects

The above method can be used in order to evaluate human clinical trial subjects or patients that are involved in medical testing or otherwise administered any type of medicinal compound, vitamin, or dietary supplement. The test subject can be a non-human animal, including but not limited to rodents (e.g., rats, mice, rabbits, hamsters, guinea pigs), dogs, pigs, cats, non-human primates (e.g., monkeys), and non-mammals (e.g., birds, amphibians, and reptiles).

The test sample can be a biological fluid sample, including but not limited to whole blood, plasma, serum, urine, urinary sediment, broncheoalveolar lavage (BAL) fluid, lymph, cerebrospinal fluid sample, saliva, semen, breast milk, and feces derived from the test subject. It can also be a cell, cell fraction, or a cell culture. Examples include broncheoalveolar lavage (BAL) cells, erythrocytes, white blood cells, nerve cells, liver cell fractions, skin fibroblasts, bone marrow histiocytes, retinal pigment epithelial cells, chorionic villus cells, and amniotic fluid cells, derived from the test subject and in vitro cell cultures, including but not limited to human hepatocellular carcinoma cell line (HepG2), diploid rat liver epithelial cell line (ARLJ301-3), Chinese hamster lung cell line (CHL/IU), baby hamster kidney cells (BHK), human kidney adenocarcinoma cells (human 769-P), human kidney proximal tubular cells (HK-2), and mouse macrophage-like cell line (J744A). The sample can also be a whole tissue, tissue slice, or tissue fraction, including but not limited to liver, kidney, muscle, heart, blood vessels and valves, lung, spleen, lymph node, bone marrow, skin, eye, and brain, derived from the test subject. The test sample can also be isolated endocytic vesicles, such as endosomes, lysosomes, and exosomes derived from cells and tissues.

2. Sample Preparation

To prepare the above-mentioned test sample, one can use liquid samples (such as urine, plasma, serum) directly without any sample preparation for liquid/liquid extraction (see below). The pH of a liquid sample can be adjusted to stabilize compounds therein for analysis as the sample pH could affect the ratio of di-22:6-BMP, di-22:6 PG, and mono-22:6-BMP isoforms in the sample. The pH value can be 1-14. Preferably, the pH value is 4-10, or 6-8, or about 7. Also, the sample can be filtered before liquid/liquid extraction in order to remove particulates.

Solid or semisolid tissue and cell samples can also be used. In one example, such samples are first homogenized with or without the addition of water or a tissue or cell protein extraction reagent (i.e., wet sample preparation) before being extracted in the manner described below. In another example, a tissue sample is lyophilized to dehydrate and finely ground before the phospholipid extraction (i.e., dry sample preparation).

Once a sample is prepared, liquid/liquid extraction is conducted to extract isoforms of di-22:6-BMP, di-22:6 PG, and mono-22:6-BMP. To that end, one can use chloroform, methanol, isopropanol, water, ethyl acetate, acetonitrile, butanol, dichloromethane, methyl tertiary butyl ether, hexane, formic acid, or ammonium hydroxide in any solvent combination or individual usage thereof. Aqueous solutions of different salts ($CaCl_2$, $MgCl_2$, NaCl, or KCl) can also be used for extracting phospholipids. Antioxidants, such as 2,6-di-tert-butyl-4-methylphenol (BHT) or vitamin E, can be added to extraction mixtures to help suppress auto oxidation of the unsaturated bonds of fatty acid groups. The extracted sample matrix containing the di-22:6-BMP and di-22:6-PG is removed and dried under a stream of nitrogen gas. The dried sample is reconstituted in an appropriate solvent, such as a mixture of acetonitrile, methanol, and water, in preparation for analysis by liquid chromatography with mass spectrometry (LC-MS, LC-MS/MS).

Sample purification generally is not required in order to further isolate the di-22:6-BMP, di-22:6 PG, and mono-22:6-BMP species from the extraction matrix. However, as the number of other competing phospholipids in the sample matrix can affect the analytical sensitivity of the di-22:6-BMP, di-22:6 PG, and mono-22:6-BMP species, removing as many competing compounds from the sample matrix as possible can enhance the analytical sensitivity. For that purpose, one can used chemical sorbents (e.g., cerium-modified columns, Tandem Labs, Salt Lake City, Utah) or anti phospholipid antibody columns. One can also use ion exchange column chromatography. For example, he or she can use preparative DEAE or LiChrospher Si-100 columns. Diethylaminoethyl (DEAE) cellulose acetate columns can be used to separate tissue phospholipids into acidic and non acidic fractions. Lipid extracts can also be separated into different phospholipid classes using LiChrospher Si-100 columns. These techniques can be applied to isolate the total fraction of BMP and PG from other competing phospholipid classes before the evaluation of specific species of di-22:6-BMP, di-22:6 PG, and mono-22:6-BMP.

One and two-dimensional thin layer chromatography (TLC) are common techniques used for phospholipid analysis. Although TLC cannot be used to separate the individual isoforms of di-22:6-BMP, di-22:6 PG, and mono-22:6-BMP, it can be used as a first step to isolate the total fraction of BMP and PG from other phospholipid classes in a test sample. The BMP and PG molecular species and isoforms can subsequently be analyzed using other techniques, such as LC-MS and GC-MS as described below.

It is not required to label or derivatize di-22:6-BMP, di-22:6 PG, and mono-22:6-BMP for analysis by liquid chromatography with mass spectrometry (e.g., LC-MS and LC-MS/MS). However, analysis of di-22:6-BMP and di-22:6-PG by immunological affinity methods (see below) would require different labeling procedures (e.g., radio label for radio immunoassay; florescent label for immunoflorescence study) and specific antibodies. Analysis of di-22:6-BMP and di-22:6-PG by gas chromatography with mass spectrometry (GC-MS, GC-MS/MS) would require derivatization of the fatty acid chains.

3. Evaluation of di-22:6-BMP, di-22:6 PG, and mono-22:6-BMP

A number of methods can be used to evaluate the abundance or localization of di-22:6-BMP, di-22:6 PG, and mono-22:6-BMP in a test sample. Examples include thin layer chromatography, liquid chromatography, gas chromatography, mass spectrometry, florescence or UV detection, scintillation counting, ELISA, NMR, imaging techniques, and labeling with a dye, antibody, florescence tag, or chemical modifier.

4. Evaluation of Individual Isoforms of di-22:6-BMP, di-22:6 PG, and mono-22:6-BMP Liquid chromatography with mass spectrometry can be used to evaluate individual isoforms of di-22:6-BMP, di-22:6 PG, and mono-22:6-BMP. One can use high performance liquid chromatography (HPLC) with quadrupole time of flight mass spectrometry (TOF-MS) and tandem mass spectrometry (TOF-MS/MS) in order to evaluate the levels of the di-22:6-BMP and di-22:6 PG isoforms in a biological sample.

In one example, one can use the chromatography column "Synergi Hydro RP" (Phenomenex, Torrance, Calif.), which is a C18 type reverse phase analytical column. For that purpose, a mixture of methanol, water, ammonium hydroxide, and formic acid can be used for Mobile Phase 1 and a mixture of methanol, hexane, ammonium hydroxide and formic acid can be used for Mobile Phase 2. An MDS Sciex API QStar quadrupole time-of-flight (Q-TOF) mass spectrometer (Applied Biosystems, Foster City, Calif.) can be used to analyze the isoforms of di-22:6-BMP, di-22:6 PG, and mono-22:6-BMP, where the data is acquired in negative electrospray ionization (ESI) mode, i.e., the di-22:6-BMP, di-22:6 PG, and mono-22:6-BMP isoforms are de-protonated.

One can also use another type of HPLC column (e.g., reverse-phase, ion exchange, normal-phase columns) or mobile phase system in order to achieve a better separation of the di-22:6-BMP, di-22:6 PG, and mono-22:6-BMP isoforms for a particular type of test sample Mass spectrometry is a common tool to profile specific phospholipid species. In addition to TOF-MS and TOF-MS/MS, other types of mass spectrometers can be used to evaluate di-22:6-BMP, di-22:6 PG, and mono-22:6-BMP in test samples. Mass spectrometers have three basic parts: an ion source, a mass analyzer, and a detector. An electrospray ionization source is most commonly used in LC-MS. Another type of ionization source that can be used for di-22:6-BMP, di-22:6 PG, and mono-22:6-BMP analysis is matrix-assisted laser desorption ionization (MALDI). Several types of mass analyzers can be used for the analysis of individual di-22:6-BMP di-22:6 PG, and mono-22:6-BMP isoforms, including triple quadrupole (TSQ MS), quadrupole time of flight, quadrupole ion trap mass spectrometers, fourier transform ion cyclotron resonance, and orbitrap mass analyzers.

Gas chromatography with mass spectrometry (GC-MS) and tandem mass spectrometry (GC-MS/MS) are used in many lipid studies. For example, GC-MS/MS can be used to monitor the specific molecular species and stereo isoforms of phosphatidylglycerol (PG) (Fritz et al. Journal of Biological Chemistry 2007; 282(7):4613-4625). A similar GC-MS technique could be extended to monitor the isoforms of di-22:6-BMP, di-22:6 PG, and mono-22:6-BMP in biological samples for phospholipidosis prediction. In that case, chemical derivatization of the di-22:6-BMP, di-22:6 PG, and mono-22:6-BMP isoforms would be required for GC-MS and GC-MS/MS studies.

Phospholipids can be detected by UV absorption at 205 nm (Patton et al. Journal of Lipid Research 1982; 23:190-196). With a preparative method to first isolate total BMP from other phospholipid classes (as described above), one can evaluate the isoforms of di-22:6-BMP and di-22:6-PG by LC separation with UV detection. Antibody-based detection methods, such as ELISA, immunoflorescence, and RIA, can also be used. Anti phospholipid antibodies for di-22:6-BMP, di-22:6 PG, and mono-22:6-BMP can be generated by standard methods and used in order to evaluate the levels of different di-22:6-BMP di-22:6 PG, and mono-22:6-BMP isoforms by ELISA, immunoflorescence, and radio immunoassays (RIA).

5. Data Normalization

It may be of interest to normalize the levels of the di-22:6-BMP, di-22:6 PG, and mono-22:6-BMP among test samples. In one example, the levels of di-22:6-BMP, di-22:6 PG, and mono-22:6-BMP in urine can be normalized based on total urine volume collected over a specified period of time, or markers of kidney function such, blood urea nitrogen, serum, or urinary creatinine In another example, the levels of di-22:6-BMP, di-22:6 PG, and mono-22:6-BMP in test samples can be normalized based on tissue weight, total protein (e.g., BCA protein assay) or total phosphorus assays.

Test Compounds

The above-described methods can be used to evaluate or monitor the phospholipidosis-inducing effects of various compounds, such as drug candidates, approved drugs, vitamins, and dietary supplements. More than 50 cationic amphiphilic drugs (CADs), including antidepressants, antianginal, antimalarial, and cholesterol-lowering agents, have been reported to induce phospholipidosis. Some examples of drugs that induce phospholipidosis include amiodarone (and its major metabolite desethylamiodarone), azithromycin, chloroquine, perhexiline, gentamicin, fluoxetine, chlorpromazine, perhexline, benzamide, erythromycin, amikacin, netilmicin, tobramycin, trospectromycin, ambroxol, bromhexine, clozapine, tilarone, boxidine, triparanol, Iprindole, zimelidine, sertraline, imipramine, chlocyclizine, meclizine, norchlorcyclizine, hydroxyzine, and liposome chemotherapeutic agents. The method described herein can be used to monitor the phospholipidosis induced by such test compounds.

Patient Management

As mentioned above, many drugs that cause phospholipidosis in animals are associated with unwanted clinical side effects, such as drug-induced QT prolongation, myopathy, hepatotoxicity, pulmonary dysfunction, or kidney toxicity. Accordingly, this invention features a method for managing patient treatment. The method includes identifying a patient under, or in need of, a treatment for a condition; obtaining a biological sample from the patient; and determining the level of a first biomarker in the biological sample as describe above. The patient is determined to be not suitable for the treatment if the level of the first biomarker is at or above a predetermined value.

1. Cardiotoxicity

The method can be used to monitor phospholipidosis in patients with the potential to develop cardiotoxicity in response to a test compound. For example, drug induced QT prolongation is a major drug safety concern because of its association with polymorphic ventricular tachycardia (torsade de pointes, TdP) and sudden death. Many approved drugs that cause phospholipidosis in animal and human tissues also cause QT prolongation in clinical studies (Table 1). The absence of a means to monitor phospholipidosis in cardiac tissues has frustrated efforts to determine the importance of drug-induced phospholipidosis in the occurrence of QT prolongation and TdP. This invention provides a means to better define the role of phospholipidosis in cardiotoxicity.

TABLE 1

Examples of drugs that cause phospholipidosis and QT prolongation

| Therapeutic Class | Exemplary Drugs |
| --- | --- |
| Antiarrhythmic | Amiodarone |
| Antimalarial | Chloroquine |
| Antibiotic | Telithromycin, Erythromycin, Azithromycin |
| Antimicrobial | Pentamidine |
| Antipsychotic | Haloperidol, Chlorpromazine |
| Antidepressant | Imipramine, Fluoxetine |

2. Myopathy

A number of anti-malarial compounds (e.g., chloroquine, hydroxychloroquine, mefloquine, quinine, quinidine) cause phospholipidosis, myopathy and neurological damage in humans and animals models. Myopathy and neurological damage also occur with other known phospholipidosis drugs, including amiodarone, haloperidol, and Coragil. Drug-induced myopathy can be difficult to diagnose because the condition is often masked by underlying skeletal muscular disease. The detection of myeloid bodies by muscle biopsy is currently required to confirm the diagnosis of myopathy caused by anti-malarials. The measurement of di-C22:6-BMP, di-22:6 PG, and mono-22:6-BMP isoforms as disclosed herein provides a non-invasive means for screening and research on the role of phospholipidosis in the etiology of drug-induced myopathies.

3. Renal Toxicity

The methods disclosed herein can also be used to better understand the simultaneous occurrence of phospholipidosis with the renal toxicities of a test compound. For example, the prolonged treatment or increased dosing of aminoglycoside antibiotics (e.g., gentamicin, tobramycin, netilmicin, and amikacin) and chloroquine in animals and humans can result in kidney damage. The relationship between phospholipidosis and the renal toxicities of drugs are not fully understood. The isoforms of di-22:6-BMP, di-22:6 PG, and mono-22:6-BMP can be used in order to investigate the temporal associations of phospholipidosis and the renal toxicities of test compounds in humans and other test subjects.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example 1

The relationship between amiodarone, azithromycin, or citalopram exposure and the occurrence of drug-induced phospholipidosis was investigated in Fisher rats. Rats were treated with amiodarone (50 mg/kg/day), azithromycin (100 mg/kg/day), citalopram (90 mg/kg/day), or no drug for 4-weeks. Urine samples were collected from each animal and prepared for analysis using a liquid/liquid extraction method. The urine samples (200 µl urine per rat) were mixed with cold 3:1 chloroform/methanol (v/v) (400 µl) and vortexed before adding 0.1% formic acid (aq.) (100 µl). The samples were vortexed again, allowed to sit for 5 min, and centrifuged for 15 min. The bottom (organic) layer was carefully removed and concentrated to dryness. The samples were reconstituted to 30 µl with 0.05% formic acid in 2:1 acetonitrile/methanol (v/v).

The molecular profile of each urine sample was acquired using liquid chromatography coupled to mass spectrometry (LC/MS). Injections were made onto a 150×2.00 mm Synergi Hydro-RP column (Phenomenex, Torrance, Calif., USA) using an a Gilson 235 auto-injector (Gilson, Inc., Middletown, Wis., USA) and an Agilent 1100 binary pump (Agilent Technologies, Palo Alto, Calif., USA). Mobile phase A was 0.25% ammonium hydroxide, 0.05% formic acid in 88:12 methanol/water (v/v). Mobile phase B was 0.25% ammonium hydroxide, 0.05% formic acid in 80:20 methanol/hexane (v/v). The flow rate was 0.25 ml/min. Initial conditions were 60% A and 40% B. The % B was increased to 90% over a 15 min period.

An MDS Sciex API QStar Pulsar quadrupole time-of-flight (Q-TOF) mass spectrometer (Applied Biosystems, Foster City, Calif.) was used for detection. Data were acquired in full scan TOF MS mode (m/z 100 to 2000) with negative electrospray ionization (ESI). The Turbo IonSpray interface was set at 425° C. and maintained at an ionspray voltage of −4.2 kV with a declustering potential of −50 V. Ionization was assisted with a nebulizer and ionspray gas (nitrogen) set at 55 and 75 (arbitrary units) respectively.

Figure 4:
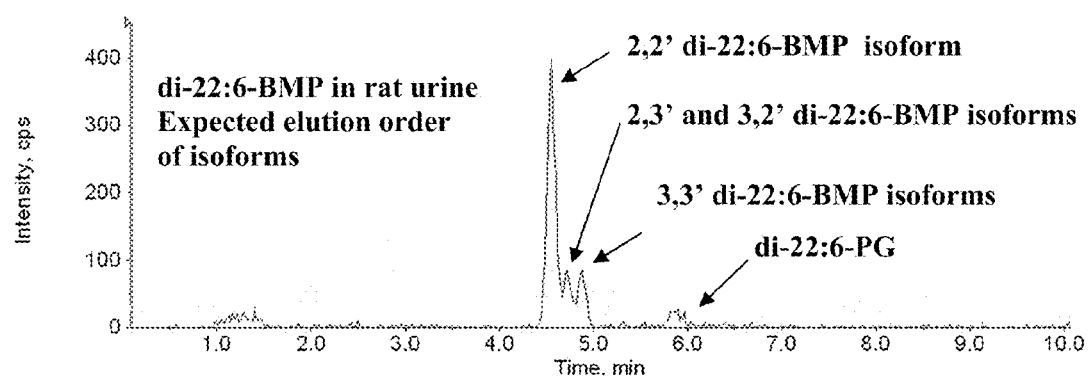
FIG. 4 is a LC-MS analysis of different di-22:6-BMP species/isoforms and di-22:6-PG in rat urine.
Figure 5A:
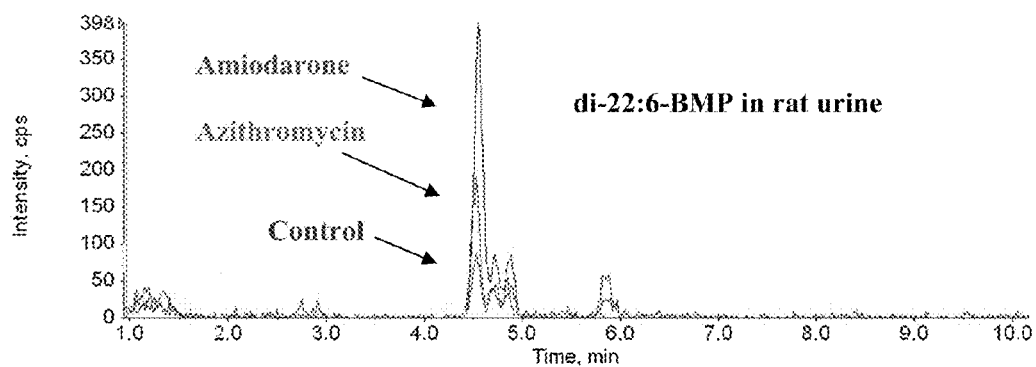
FIGS. 5A and 5B are LC-MS analyses of different di-22:6-BMP species/isoforms in urine of rats treated with amiodarone (4A), azithromycin (4A), or citalopram (4B).
Figure 5B:
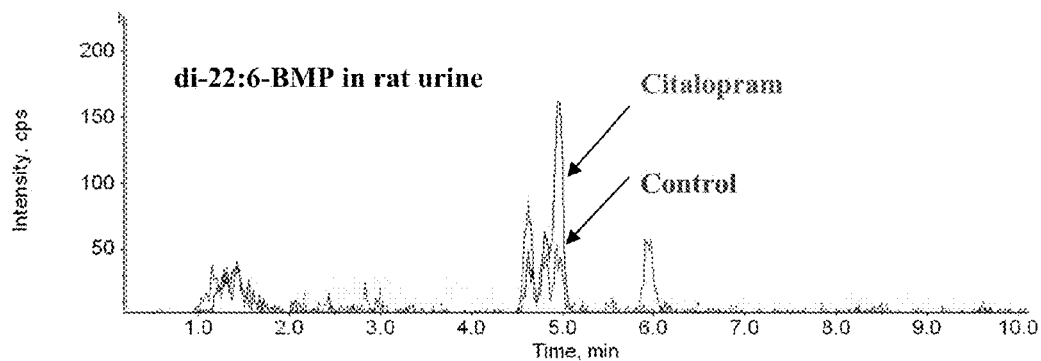

The results are shown in FIGS. 4, 5A, and 5B. As shown in FIG. 4, the LC-MS method unexpectedly resolved the different di-22:6-BMP and di-22:6-PG isoforms well. It was found that the 2,2' isoform of di-22:6-BMP eluted from the HPLC first, followed by the 2,3' and 3,2' isoforms, and then the 3,3' isoform. It was also unexpected that treatment with amiodarone and azithromycin resulted in a significant increase in the first eluting isoform of di-22:6-BMP (i.e., 2,2' di-22:6-BMP) and a lesser increase in the other isoforms (i.e., 3,2' di-22:6-BMP, 2,3' di-22:6-BMP, and 3,3' di-22:6-BMP) (FIG. 5A). On the other hand, treatment with citalopram unexpectedly resulted in an increase in the last eluting isoform of di-22:6-BMP (i.e., 3,3'di-22:6-BMP) but no significant change in the other isoforms (FIG. 5B).

These results demonstrate that drugs can have differential effects on the levels of different di-22:6-BMP isoforms in rat urine. They also demonstrated that the di-22:6-BMP isoforms can be used, individually or/and in combination, as biomarkers for evaluating the potential of a test compound to induce phospholipidosis in a target subject.

A major challenge in risk assessment is tracking the onset and time course of phospholipidosis with drug toxicities. The method of this invention, which determines the levels of different di-22:6-BMP, di-22:6-PG, and mono-22:6-BMP isoforms, can be used to monitor the onset, time course, and intensity of phospholipidosis in relation to the toxicities of drugs.

Example 2

Another challenge in phospholipidosis risk assessment is determining which type of cells and tissues in the body are affected. This example demonstrates that a specific species of phosphatidylglycerol (PG), di-docosahexaenoyl (C22:6)-PG (di-22:6-PG), correlates with the amiodarone phospholipidosis in rats. Accordingly, a method using di-22:6-PG in combination with different isoforms of di-22:6-BMP and mono-22:6-BMP can be used to specifically detect phospholipidosis of the lung as the lung secretes high amount of PG as lung surfactant.

Figure 6:
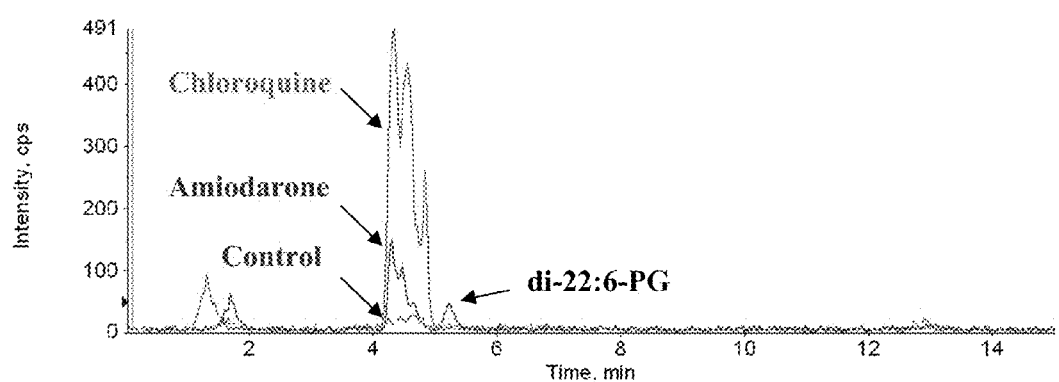
FIG. 6 is a LC-MS analysis of di-22:6-BMP and di-22:6-PG isoforms in urine of rats treated with chloroquine and amiodarone.
Figure 7:
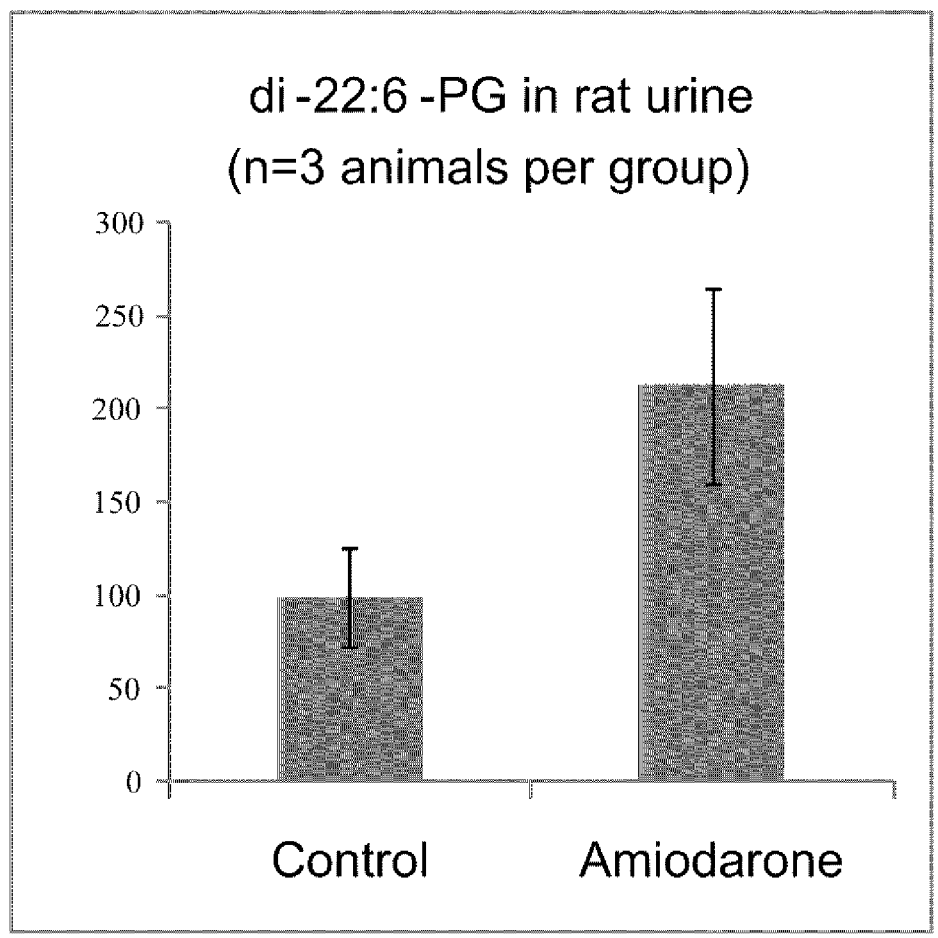
FIG. 7 is a diagram showing the intensity of di-22:6-PG in urine of rats treated with amiodarone.

Briefly, rats were administered amiodarone, chloroquine, or no drug (vehicle). Urine was collected from each rat and examined for levels of di-22:6-PG in the manner described above. As shown in FIGS. 6 and 7, it was found that the level of di-22:6-PG increased in the urine of rats treated with amiodarone (a compound well known to cause pulmonary phospholipidosis and toxicity), but not in the urine of rats treated with chloroquine, or no drug. In addition, patients with amiodarone pulmonary toxicity show significant increases in total BMP (+64%) and total PG (+1866%) in bronchoalveolar lavage (BAL) cells compared to control subjects, whereas the relative composition of other phospholipids remain unchanged (Martin and Standing, Pharmacology and Experimental Therapeutics 1988; 244(2):774-779). These results demonstrate that different isoforms of di-22:6-BMP, di-22:6-PG, and mono-22:6-BMP provide a means to gain a better overall picture of the effects of phospholipidosis in the lungs.

Similarly, the above-described method can be used in combination with other phospholipid biomarkers to specifically determine other organs that are affected by phospholipidosis. For example, an increase in di-22:6-BMP, di-22:6-PG, and mono-22:6-BMP accompanied by an increase in phosphatidylinositol (PI), phosphatidylethanolamine (PE) and phosphatidylcholine (PC) biomarkers may be used to specifically detect phospholipidosis of the kidney. As another example, a method using the species of di-22:6-BMP, di-22:6-PG, and mono-22:6-BMP in combination with species of lysophosphatidylcholine (LPC) or total LPC may be used to specifically detect phospholipdosis of the liver.

Example 3

Male Sprague-Dawley rats were administered amiodarone (150 mg/kg), chloroquine (120 mg/kg), test compound A (50 mg/kg), or 0.5% Methylcellulose (vehicle/control), once daily for 14 consecutive days. Urine samples were collected from each animal ~6-12 hours post-dose on days 4 and 10 and subjected to the assay described above.

The results are shown in FIGS. 8A and 8B. Following treatment with amiodarone (150 mg/kg/day), chloroquine (120 mg/kg/day) and compound A (50 mg/kg/day), the urinary levels of di-C22:6-BMP increased approximately 0.14 (114%), 3.4 (344%), and 10 (1004%) fold, respectively, by Day 4, and 3 (317%), 6 (605%), and 20 (2035%) fold, respectively, by Day 10. As the measurement of di-C22:6-BMP in urine samples is non-invasive, it is especially useful for assessing the temporal relationship between phospholipidosis and the toxicities of drugs.

Example 4

Figure 9:
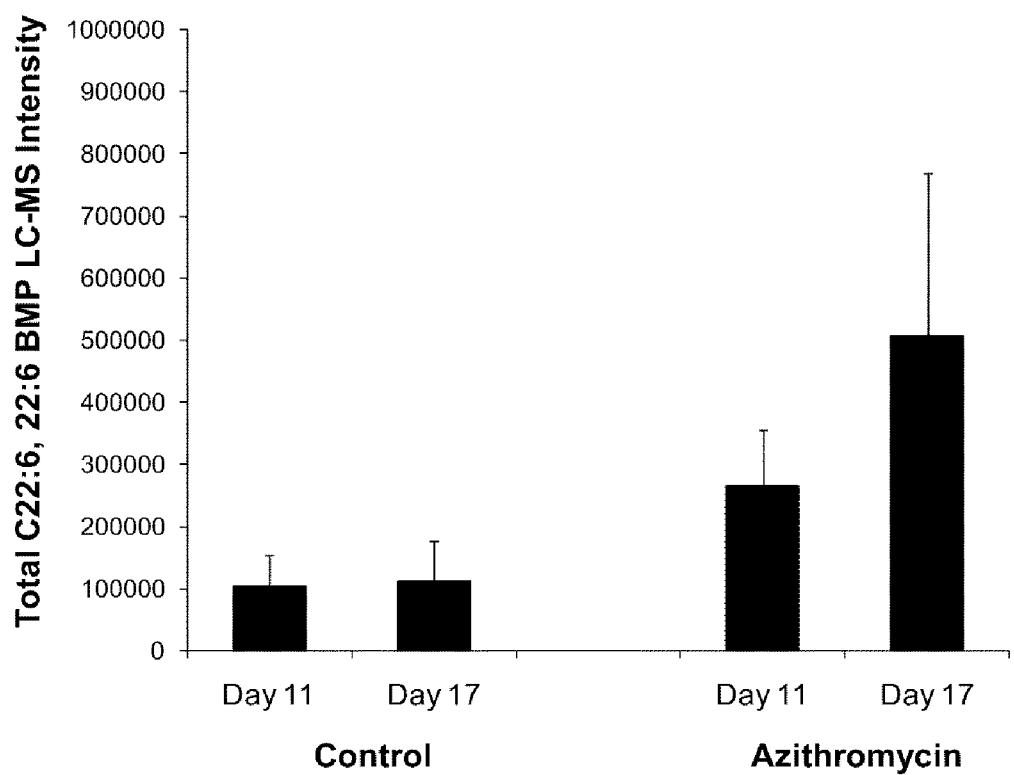
FIG. 9 is a diagram showing the levels of di-C22:6-BMP (including all isoforms) in the urine of Sprague-Dawley rats following azithromycin treatment.

The methods described above were used to evaluate the tissue phospholipidosis induced by azithromycin (150 mg/kg/day) in rats over a 17-day period. Urine samples were collected from the rats on Days 11 and 17 and subjected to the assay. Results showed that urine from the rats treated with azithromycin contained more di-C22:6-BMP compared to those from the rats that received no drug (controls). See FIG. 9. On Day 11, the mean level (n=5 rats per group) of di-C22: 6-BMP in urine was increased by 2.6-fold in the rats treated with azithromycin compared to the controls. On Day 17, the mean level (n=5 rats per group) of di-C22:6-BMP in urine was increased approximately by 4.5-fold in the azithromycin treated rats compared to the control rats.

Example 5

Sprague-Dawley rats were treated with a test compound (Compound B) that induces phospholipidosis in the lung. Lung tissue samples were collected from each animal and prepared for analysis using a liquid/liquid extraction method. The lung samples (0.25 g per rat) were mixed with cold 90:20 ethyl acetate/methanol (v/v) with 0.1% formic acid (500 µl). The samples were vortexed, allowed to sit for 5 min, vortexed again and then centrifuged for 15 min. The top layer was carefully removed and concentrated to dryness. The samples were reconstituted to 50 µl with 0.25% ammonium hydroxide, 0.05% formic acid in 88:12 methanol/water (v/v) and analyzed by LC-MS as described above.

Figure 10:
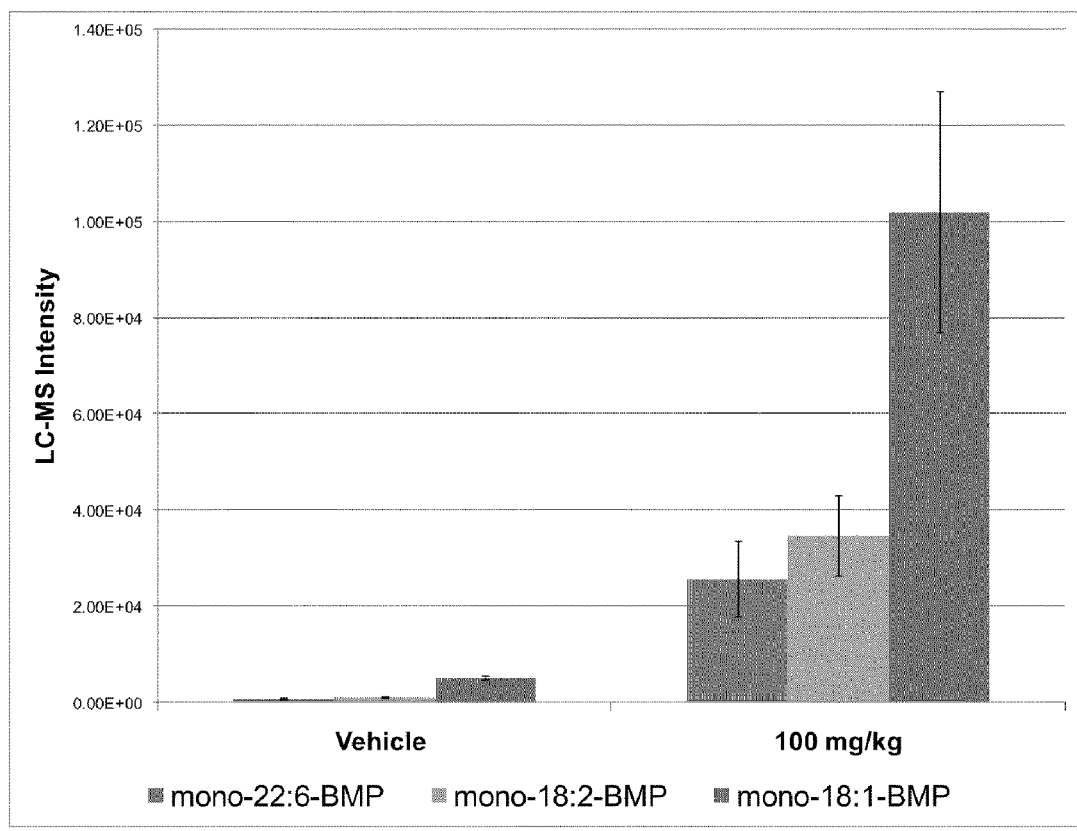
FIG. 10. is a diagram showing the levels of mono-22:6-BMP, mono-18:1-BMP, and mono-18:2-BMP isoforms in the lung tissue of rats treated with test Compound ABC compared to rats treated with no drug (vehicle).

The results are shown in FIG. 10. The levels of mono-22: 6-BMP, mono-18:1-BMP, and mono-18:2-BMP isoforms were increased in the lung tissue of the rats treated with Compound ABC, but not the rats treated with no drug (vehicle).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. A method for evaluating the activity of a test compound to induce phospholipidosis in a target subject, comprising obtaining (1) a test sample from a test subject that has been administered a test compound, (2) a population of test cells that have been contacted with the test compound, or (3) endocytic vesicles isolated from the test sample or the test cells, determining the level of each of a group of biomarkers in the test sample, the cells, or the endocytic vesicles, wherein the group of biomarkers includes 2,2' di-22:6-BMP, 3,2' di-22:6-BMP, 2,3' di-22:6-BMP, and 3,3'di-22:6-BMP, and optionally includes di-22:6-PG, 2-mono-22:6-BMP, or 3-mono-22:6-BMP, and comparing the level of each biomarker with a corresponding predetermined level for the same biomarker, the predetermined level being obtained, for (1), from a control sample from a control subject who has not been administered the test compound, for (2), from a control cell that has not been contacted with the test compound, or for (3), from endocytic vesicles isolated from the control sample or the control cells, wherein the test compound is determined to have the activity to induce phospholipidosis in the target subject if the level of any of the group of biomarkers is at or above the corresponding pre-determined level.

2. The method of claim 1, wherein the target subject is a human.

3. The method of claim 1, wherein the test subject is a rodent, a dog, a pig, a non-human primate, or a human.

4. The method of claim 1, wherein the test sample is a whole blood sample, a plasma sample, a serum sample, an urine sample, an urinary sediment sample, a broncheoalveolar lavage fluid sample, a lymph sample, a cerebrospinal fluid sample, a saliva sample, a semen sample, a breast milk sample, a feces sample, or a tissue sample from liver, kidney, muscle, heart, blood vessels and valves, lung, spleen, lymph node, bone marrow, skin, eye, or brain.

5. The method of claim 1, wherein the population of test cells comprises broncheoalveolar lavage cells, erythrocytes, white blood cells, nerve cells, liver cell fractions, skin fibroblasts, bone marrow histiocytes, chorionic villus cells, retinal pigment epithelial cells, amniotic fluid cells, cells of human hepatocellular carcinoma cell line (HepG2), diploid rat liver epithelial cell line (ARLJ301-3), Chinese hamster lung cell line (CHL/IU), baby hamster kidney cells (BHK), human kidney adenocarcinoma cells (human 769-P), human kidney proximal tubular cells (HK-2) or mouse macrophage-like cell line (J744A).

6. The method of claim 1, wherein the endocytic vesicles are endosomes, lysosomes, or exosomes.

7. The method of claim 3, wherein the pre-determined level for each biomarker is obtained from a control subject who has not been administered the test compound.

8. The method of claim 5, wherein the pre-determined level for each biomarker is obtained from a control cell that has not been contacted with the test compound.

9. The method of claim 1, wherein the group of biomarkers includes di-22:6-PG, 2-mono-22:6-BMP, or 3-mono-22:6-BMP.

10. The method of claim 9, wherein the group of biomarkers includes 22:6-PG, 2-mono-22:6-BMP, and 3-mono-22: 6-BMP.

11. The method of claim 1, wherein the method further comprises determining the level of an additional species of BMP, the total BMP, or the fatty acid classification of total BMP.

12. The method of claim 1, wherein the determining step is conducted by LC-MS, LC-MS/MS, GC-MS, GC-MS/MS, or ELISA.

13. The method of claim 1, wherein the method further comprises separating 2,2' di-22:6-BMP, 3,2' di-22:6-BMP, 2,3' di-22:6-BMP, di-22:6-PG, 2-mono-22:6-BMP, and 3-mono-22:6-BMP from each other before determining their levels.

14. A method for managing patient treatment comprising
identifying a patient under a treatment suspected to induce phospholipidosis in the patient,
obtaining a test sample from the patient,
determining the level of each of a group of biomarkers in the test sample, wherein the group of biomarkers includes 2,2' di-22:6-BMP, 3,2' di-22:6-BMP, 2,3' di-22:6-BMP, and 3,3'di-22:6-BMP, and optionally includes di-22:6-PG, 2-mono-22:6-BMP, or 3-mono-22:6-BMP, and
comparing the level of each biomarker with a corresponding pre-determined level for the same biomarker, the pre-determined level being obtained from a control sample from a control subject who has phospholipidosis,
wherein the patient is determined to be not suitable for the treatment if the level of any of the group of biomarkers is at or above the corresponding predetermined level.

15. The method of claim 14, wherein there the method further comprises separating 2,2' 22:6-di-BMP, 3,2' 22:6-di-BMP, 2,3' 22:6-di-BMP, 3,3'di-22:6-BMP, and di-22:6-PG from each other before determining their levels.

16. A method of diagnosing a lipid storage disorder in a human subject, the method comprising:
obtaining a test sample from the subject;
determining the level of each of a group of biomarkers in the test sample, wherein the group of biomarkers includes 2,2' di-22:6-BMP, 3,2' di-22:6-BMP, 2,3' di-22:6-BMP, and 3,3'di-22:6-BMP, and optionally includes di-22:6-PG, 2-mono-22:6-BMP, or 3-mono-22:6-BMP, and
comparing the level of each biomarker with a corresponding pre-determined level for the same biomarker, the pre-determined level being obtained from a control sample from a control subject who has the lipid storage disorder,
wherein having a level of any of the group of biomarkers that is at or above the corresponding predetermined level indicates that the subject has or is at risk of developing the lipid storage disorder.

17. The method of claim 16, wherein the disorder is Niemann-Pick Type C (NPC) disease and the pre-determined level for each biomarker is obtained from a control subject that has Niemann-Pick Type C (NPC) disease.

18. The method of claim 16, wherein the method further comprises separating of 2,2' 22:6-di-BMP, 3,2' 22:6-di-BMP, 2,3' 22:6-di-BMP, 3,3'di-22:6-BMP, and di-22:6-PG from each other before determining their levels.

19. The method of claim 14, wherein the group of biomarkers includes di-22:6-PG, 2-mono-22:6-BMP, or 3-mono-22:6-BMP.

20. The method of claim 16, wherein the group of biomarkers includes di-22:6-PG, 2-mono-22:6-BMP, or 3-mono-22:6-BMP.

* * * * *